United States Patent
Seo et al.

(10) Patent No.: US 7,097,882 B2
(45) Date of Patent: Aug. 29, 2006

(54) SUBSTRATE FOR IMMOBILIZING PHYSIOLOGICAL MATERIAL, AND METHOD OF FABRICATING SAME

(75) Inventors: Kang-Il Seo, Suwon (KR); Ji-Na Namgoong, Yongin (KR); Eun-Keu Oh, Suwon (KR); Young-Do Choi, Bucheon (KR); In-Ho Lee, Incheon (KR); Tai-Jun Park, Seoul (KR); Hun-Soo Kim, Seoul (KR)

(73) Assignee: Samsung SDI Co., Ltd., Suwon (KR)

( * ) Notice: Subject to any disclaimer, the term of this patent is extended or adjusted under 35 U.S.C. 154(b) by 317 days.

(21) Appl. No.: 10/107,721

(22) Filed: Mar. 26, 2002

(65) Prior Publication Data

US 2003/0072951 A1     Apr. 17, 2003

Related U.S. Application Data

(60) Provisional application No. 60/344,415, filed on Dec. 28, 2001.

(30) Foreign Application Priority Data

Aug. 21, 2001 (KR) ............... 2001-50481

(51) Int. Cl.
  B05D 3/10    (2006.01)
  B05D 3/02    (2006.01)
(52) U.S. Cl. .......... 427/333; 427/340; 427/385.5
(58) Field of Classification Search ............ 427/333, 427/340, 385.5
  See application file for complete search history.

(56) References Cited

U.S. PATENT DOCUMENTS

| | | | |
|---|---|---|---|
| 5,063,081 A * | 11/1991 | Cozzette et al. .......... 435/4 |
| 5,858,653 A | 1/1999 | Duran et al. | |
| 5,869,272 A | 2/1999 | Bogart et al. | |
| 5,919,523 A | 7/1999 | Sundberg et al. | |
| 5,981,734 A | 11/1999 | Mirzabekov et al. | |
| 5,985,551 A | 11/1999 | Brennan | |
| 6,319,674 B1 | 11/2001 | Fulcrand et al. | |
| 6,951,682 B1 * | 10/2005 | Zebala .............. 428/312.2 |
| 2004/0092396 A1 * | 5/2004 | Glazer et al. ............ 502/439 |

FOREIGN PATENT DOCUMENTS

| | | |
|---|---|---|
| GB | 2 342 866 A | 11/1998 |
| KR | 2001 0096721 A | 11/2001 |
| WO | WO 99/40038 | 8/1999 |

OTHER PUBLICATIONS

Corresponding EPO application Search Report dated Jun. 3, 2003.

* cited by examiner

*Primary Examiner*—Jezia Riley
(74) *Attorney, Agent, or Firm*—Christie, Parker & Hale, LLP

(57) ABSTRACT

A substrate for immobilizing a physiological material is provided. The substrate comprises a substrate material; a primer layer formed on the substrate material; and an immobilization layer formed on the primer layer. The primer layer is capable of enhancing the attachment between the substrate and the immobilization layer. The substrate for immobilizing a physiological material can provide the immobilization layer with a stable, uniform, and high density through a simple process.

31 Claims, 5 Drawing Sheets

(a)　　　(b)

(a)　　　(b)

SUBSTRATE FOR IMMOBILIZING PHYSIOLOGICAL MATERIAL, AND METHOD OF FABRICATING SAME

CROSS-REFERENCE TO RELATED APPLICATION

This application claims priority of U.S. Provisional Patent Application No. 60/344,415, filed Dec. 28, 2001, and claims priority of Korean Patent Application No. 2001-50481, Filed Aug. 21, 2001 the entire disclosures of which are incorporated herein by reference.

FIELD OF THE INVENTION

The present invention relates to a substrate for immobilizing a physiological material and a method of preparing the same, and more particularly, to a substrate for immobilizing a physiological material having a functional group with a uniform and high density and a method of fabricating the same.

BACKGROUND OF THE INVENTION

Recently, demands for the development of technology used for analyzing the activity of physiological materials, such as nucleic acids, proteins, enzymes, antibodies, and antigens have rapidly increased in the world. For such demands, a biochip in which the required physiological material molecules are immobilized on certain tiny regions by adopting semiconductor processing techniques is suggested, so thereby physiologically useful information is easily obtained just by biochemically searching the biochip.

The biochip is in the form of a conventional semiconductor chip, but what is integrated thereon is a bio-organic material such as an enzyme, a protein, an antibody, DNA, a microorganism, animal and plant cells and organs, a neuron, and so on. The biochip can be classified into a "DNA chip" immobilizing a DNA probe, a "protein chip" immobilizing a protein such as an enzyme, an antibody, an antigen and so on, and a "lab-on-a-chip" which is integrated with pre-treating, biochemical reacting, detecting, and data-analyzing functions to impart an auto-analysis function.

To achieve the successful development of such a biochip, it is important to find a method for immobilizing a physiological material in which an interface between the physiological material and a substrate is efficiently formed, and the inherent functions of the physiological material can be utilized at a maximum level. Generally, the physiological material is immobilized on the surface of a glass slide, a silicon wafer, a microwell plate, a tube, a spherical bead, a surface with a porous layer, etc. by various techniques, for example, by reacting DNA with carbodiimide to activate a 5'-phosphate group of DNA, and by reacting the activated DNA with a functional group on the surface of the substrate so as to immobilize the DNA on the substrate.

U.S. Pat. No. 5,858,653 discloses a composition comprising an ion group, such as a quaternary ammonium group, a protonated tertiary amine, or phosphonium, capable of reacting with a target physiological material, and a polymer having a photo-reactive group or a thermochemically reactive group for use in attaching to the surface of substrate. U.S. Pat. No. 5,981,734 teaches that when DNA is immobilized by a polyacrylamide gel having an amino group or an aldehyde group, the DNA can be bound with a substrate via a stable hybridization bond to easily facilitate carrying out of analysis. U.S. Pat. No. 5,869,272 discloses an attachment layer comprising a chemical selected from dendrimers, star polymers, molecular self-assembling polymers, polymeric siloxanes, and film-forming latexes formed by spin-coating a silicone wafer with aminosilane. U.S. Pat. No. 5,869,272 also discloses a method for the determination of a bacteria antigen by detecting a visual color change of an optically active surface. U.S. Pat. No. 5,919,523 discloses a method for preparing a support on which an amino silane-treated substrate is doped with glycine or serine or is coated with an amine, imine, or amide-based organic polymer. U.S. Pat. No. 5,985,551 discloses a method for providing amino groups on a solid substrate by using a photolithography technique on the amino silane treated substrate, the method involving allotting hydrophilic functions on regions to immobilize DNA and fluorosiloxane hydrophobic functions on other regions so as to form a desirable patterned DNA spot on the substrate.

In the above-mentioned patents, the immobilization layer is provided by preparing a self-assembly monolayer of silane molecules. Preferably, the silane is aminoalkoxy silane since it does not produce acidic by-products, and it can provide a molecular layer having a functional group with a relatively high density. Although much research has advanced the obtainment of a uniform monolayer having high-density functional groups using aminoalkoxy silanes, an aminosilane monolayer having a functional group with a uniform and high density and shorter manufacturing time has not been achieved.

The performance of the biochip is also affected by the nature of the substrate used as a support. That is, in order to utilize a spectroscopy technique on the hybridization analysis of the very dense array, the substrate should be optically transparent and the bond between the surface of the substrate and the physiological material should be stable.

Generally, the immobilization substrate is prepared by coating a sodium lime glass with amino silane compounds. The sodium lime glass is, however, a low level glass containing more than about 12% sodium. The sodium present in such glass is easily deposited, resulting in the degeneration of the transparency of the glass and the dissociation of the siloxane bond or the bond between the glass and silane. The immobilization layer thereby looses binding strength to the substrate, and it becomes difficult to achieve a uniform density of functional groups.

To solve the problems, borosilicate or boroaluminosilicate glass is suggested in WO 99/40038, but it has the disadvantage of being too expensive.

SUMMARY OF THE INVENTION

In order to solve the problems, it is an object of the present invention to provide a substrate for immobilizing a physiological material having a functional group with a uniform and high density.

It is another object to provide a method of fabricating the substrate for immobilizing a physiological material by a simple process.

It is still another object to provide a biochip comprising the substrate for immobilizing a physiological material.

Additional objects and advantages of the invention will be set forth in part in the description which follows and, in part, will be obvious from the description, or may be learned by practice of the invention.

In order to achieve these objects, the present invention provides a substrate for immobilizing a physiological material comprising a substrate; a primer layer formed on the substrate; and an immobilization layer formed on the primer layer, wherein the primer layer is to enhance the attachment between the substrate and the immobilization layer.

The present invention further provides a method of fabricating a substrate for immobilizing a physiological material comprising: coating a substrate with a compound having a functional group to provide a primer layer; and coating the primer layer with a compound having a functional group capable of immobilizing the physiological material to provide an immobilization layer, wherein the primer layer is capable of enhancing the attachment between the substrate and the immobilization layer.

The present invention also provides a biochip comprising a physiological material immobilized on the surface of the substrate.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

Hereinafter, the present invention is described in further detail.

Figure 1:
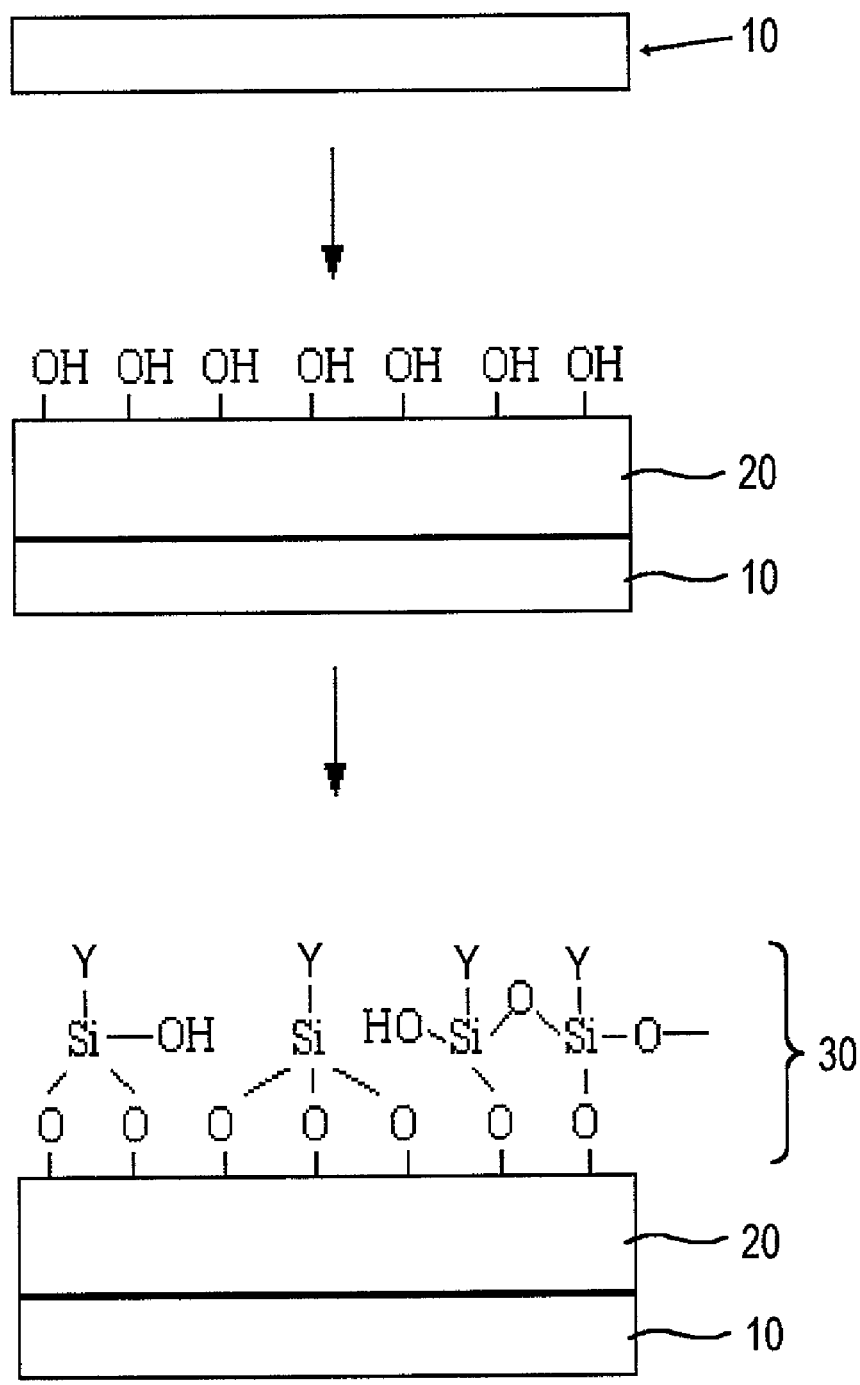
FIG. 1 is a schematic diagram illustrating a process of fabricating a substrate for immobilizing a physiological material according to the present invention.

FIG. 1 is a schematic diagram illustrating a process of fabricating a substrate for immobilizing a physiological material. As shown in FIG. 1, the substrate for immobilizing a physiological material 10 includes a primer layer 20 between the substrate 10 and an immobilization layer 30. The primer layer 20 blocks deposition of alkaline material from the substrate of a sodium lime glass and is capable of improving the attachment between the substrate 10 and the immobilizing functional group of the immobilization layer 30. It also highly reacts with aminosilane, so it imparts uniform arraying of the high-density functional group.

The substrate 10 of the present invention is exemplified by, but is not limited to, glass, a silicone wafer, polycarbonate, polystyrene, polyurethane and so on. It may also be in a form of a microwell plate, a tube, a spherical bead, or a porous layer.

Examples of the compound for forming a primer layer capable of enhancing the attachment between the substrate 10 and the immobilization layer 30 include, but are not limited to, any compound selected from the group consisting of compounds represented by the following formula 1 and formula 2 and mixtures thereof:

wherein

M is an element selected from the group consisting of 4B, 3A, 4A, and 5A group elements of the Periodic Table, and preferably selected from the group consisting of Si, Zr, Ti, Al, Sn, In, and Sb;

$R^1$ is a hydrogen atom or a $C_{1-20}$ alkyl or $C_{6-12}$ aromatic group, and is preferably a hydrogen atom or a methyl, ethyl, propyl, butyl, or phenyl; and n is a value ranging from 3 to 4 and is determined depending upon the valence of M;

wherein

M' is an element selected from the group consisting of 4B, 3A, 4A, and 5A group elements of the Periodic Table, and is preferably selected from the group consisting of Si, Zr, Ti, Al, Sn, In, and Sb;

$R^2$ is a hydroxy, a halogen atom, a $C_{1-20}$ alkoxy group or a $C_{6-12}$ oxyaromatic group, and is preferably a hydroxy, chlorine or a methoxy, ethoxy, propoxy, butoxy or phenoxy group;

$R^3$ is a methylene or a phenyl, optionally substituted with a $C_{1-6}$ substituent;

m is a value ranging from 2 to 3 and is determined depending upon the valence of M';

p is a numerical value ranging from 2 to 4; and q is a numerical value ranging from 1 to 20.

A preferred example of a compound represented by formula (1) is a silicon tetraalkoxide, such as tetraethyl orthosilicate, aluminum tributoxide, zirconium tetrabutoxide, or the like.

Examples of the compound represented by formula (2) are bis (triethoxysilyl)ethane, bis(trimethoxysilyl)hexane, bis (triethyoxysilyl)methane, 1,9-bis-(trichlorosilyl)nonane, bis (tri-n-butoxytin)methane, bis(triisopropoxytitanium)hexane, 1,4-bis(trimethoxysilylethyl)benzene, and so on.

In a case when the compound of formula (1) is used in a mixed with the compound of formula (2), the weight ratio preferably ranges from 0.01:99.9 to 100:0, more preferably from 50:50 to 95:5.

The primer layer is formed by coating the substrate with a coating composition comprising a compound capable of enhancing the attachment between the substrate and the immobilization layer. The coating composition is prepared by dissolving the compound for forming the primer layer in a dilution solvent. The dilution solvent is a mixture of water and an organic solvent, and the organic solvent is preferably an alcohol solvent such as methanol, ethanol, propanol, or butanol; a cellusolve solvent such as methyl cellusolve; any organic solvent compatible with water such as acetones; or any mixture thereof.

The compound for forming the primer layer is dissolved in the solvent and forms an oligomer via a hydrolysis reaction and a condensation reaction. In order to increase the reaction rate, any organic or inorganic acid such as acetic acid, nitric acid, hydrochloric acid, and so on is added so that the pH of the coating composition is adjusted to from 2 to 10.

The coating composition comprises the compound for forming the primer layer in an amount from 0.1 to 90 wt %, preferably from 1 to 50 wt %. In the case when the amount of the compound is less than 0.1 wt %, the enhancement of the attachment between the substrate and the immobilization layer is not sufficient, whereas in the case when it is more than 90 wt %, the coating composition cannot be applied to the substrate.

The primer layer is simply prepared by coating the substrate with the coating composition. An example of the coating method includes, but is not limited to, a wet coating method, such as dipping, spraying, spin-coating, or printing. As shown in FIG. 1, it is provided with a silanol group (SiOH) capable of binding with an immobilization functional group on the surface of the primer layer.

The coated substrate is preferably heated at the temperature ranging from 100 to 400° C. in order to increase the density of the coating layer and to enhance the attachment to the substrate. In the case when the heating temperature is less than 100° C., the surface strength is not sufficient and the alkaline material, such as sodium, is less blocked. On the other hand, in the case of a heating temperature of more than 400° C., the silanol group of the surface is degenerated so as to reduce the attachment between the coating layer and the substrate. The immobilization layer is obtained by applying the compound comprising an immobilization functional group on the surface of the primer layer so that the substrate for immobilizing a physiological material is provided. Herein, the term "immobilization layer" means the coating layer of any compound having immobilization functional groups used in immobilizing the physiological material.

The immobilization functional group is exemplified by, but is not limited to, an amino, an aldehyde, a mercapto, or a carboxyl group. The compound having the immobilization group may be represented by the following formula (3):

$$Y-R^4-Si(R^5)_3 \quad (3)$$

wherein

Y varies depending upon the terminal group of the physiological material and is at least one functional group selected from the group consisting of amino, aldehyde, mercapto, and carboxyl groups;

$R^4$ is selected from the group consisting of $C_{1-20}$ alkyl groups, $C_{6-20}$ aromatic groups, ester groups, and imine groups, and is preferably a methyl group, an ethyl group, a propyl group, or a butyl group; and $R^5$ is selected from the group consisting of hydroxyl groups, $C_{1-20}$ alkoxy groups, acetoxy groups, halogen groups, and combinations thereof, and is preferably a hydroxy ethoxyl or an acetoxyl group.

Preferred examples of the compound of formula (3) having an amino group as the immobilization functional group include 3-aminopropyltrimethoxysilane, 3-aminopropyltriethoxysilane, 2-aminoundecyltrimethoxylsilane, aminophenyltrimethoxysilane, and N-(2-aminoethylaminopropyl)trimethoxysilane. The compound having the mercapto group is preferably exemplified by 3-mercaptopropyltrimethoxysilane, 3-mercaptopropyltriethoxysilane, etc. The compound having the aldehyde group is preferably exemplified by 4-trimethoxysilylbutanal, 4-trimethoxysilylbutanal, etc. The compound having the carboxyl group is preferably exemplified by carboxymethyltrimethoxysilane, carboxymethyltriethoxysilane, etc.

In order to reduce the hydrophilicity of the immobilization group and to improve the thermal stability of the three-dimensional cross-linking structure, the compound of formula (3) may be mixed with a hydrophobic silane compound represented by the following formula (4):

wherein $R^6$ is selected from the group consisting of $C_{1-14}$ alkyl groups, $C_{6-12}$ aromatic groups optionally substituted with preferably methyl, ethyl or propyl, and $CX_3$, wherein X is halogen, and preferably, methyl, ethyl, or propyl; $R^7$ and $R^8$ are each independently selected from the group consisting of $C_{1-14}$ alkoxy groups, acetoxy groups, hydroxyl groups, and halogen groups, and is preferably methoxy, ethoxy, acetoxy or chlorine;

$R^9$ is selected from the group consisting of hydrogen, $C_{1-14}$ alkyl groups, and $C_{6-12}$ aromatic groups, and is preferably methyl or ethyl; and k is an integer ranging from 1 to 15.

The hydrophilicity, the efficiency, the amount, and the shape of the immobilization layer can be controlled by adding the hydrophobic silane compound to the compound having the immobilization functional group. The hydrophobic silane compound is exemplified by methyltrimethoxysilane, propyltriacetoxysilane, etc.

When the silane compound of formula (3) is mixed with the hydrophobic silane compound of formula (4), the weight ratio is 0.01:99.99 to 100:0, and preferably 50:50 to 95:5.

The immobilization layer is prepared by coating the primer layer with a coating composition, the coating composition being prepared by dissolving the compound of formula (3) and the optional compound of formula (4) in a dilution solvent.

The dilution solvent is an organic solvent, water, or a mixture of the organic solvent and water. The organic solvent is preferably an alcohol solvent such as methanol, ethanol, propanol, or butanol; a cellusolve solvent such as methyl cellusolve; any organic solvent compatible with water such as acetones; or any mixture thereof. Since the dilution solvent is an organic solvent compatible with water, the silane oligomer is readily co-polymerized to obtain the coating composition, and is environmentally friendly.

The coating composition for forming the immobilization layer comprises 0.1 to 90 wt %, preferably 0.1 to 50 wt % of the silane compound. When the amount of the silane compound is less than 0.1 wt %, the immobilization functional group is not sufficiently formed, whereas when it is more than 90 wt %, the coating composition cannot be applied to the substrate, and the obtained coating layer is too thick to prevent cracking.

According to one preferred embodiment of the present invention, the immobilization layer is formed by a coating composition comprising a silane oligomer and the dilution solvent, wherein the silane oligomer is obtained by copolymerizing the silane compound having the immobilization functional group in water or a mixed solvent containing water and an organic solvent. The dilution solvent is selected from the group consisting of water, organic solvent, and a mixed solvent of water and an organic solvent.

According to another preferred embodiment of the present invention, the coating composition may be obtained by mixing the silane compound having the immobilization functional group with dilution solvent selected from the group consisting of water and a mixed solvent of water and an organic solvent. The silane compound is copolymerized in water or a mixed solvent containing water and an organic solvent to form a silane oligomer.

When an amino silane compound, one of the compounds of formula (3) having an amino group as the immobilization functional group, is polymerized in water, the compound represented by the following formula (5) is obtained:

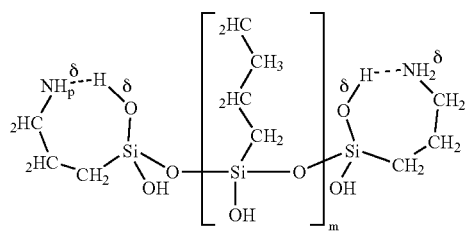

wherein r is the degree of the copolymerization.

The amino silane compound of which in the compound of formula (3) the immobilization functional group is an amino group is polymerized together with the hydrophobic silane compound of formula (4) to provide the amino silane oligomer represented by the following formula (6):

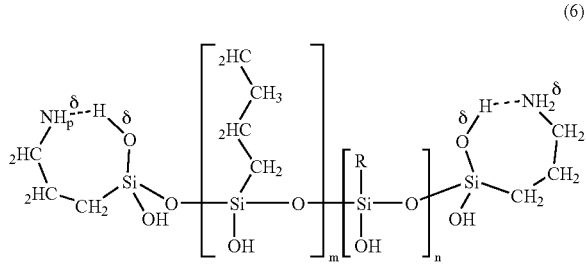

wherein
$R^6$ is the same as defined in formula (4), and
s and t are respectively degrees of copolymerization.

In order to increase the reaction rate, any organic or inorganic acid catalyst, such as acetic acid, nitric acid, hydrochloric acid and so on, is added so that the pH of the coating composition is adjusted to at or between 2 and 10. The copolymerization reaction is preferably carried out at temperature of 0° C. to 100° C. for 1 to 24 hours.

The silane oligomer maintains a stable reaction equivalent rate so as to not participate in a further reaction since the terminal amino group is bound with the terminal hydroxyl group via a hydrogen bond in the coating composition as shown in formulae (5) and (6).

Further, according to other preferable embodiments of the present invention, the silane compound having the immobilization functional group is dissolved in the water or a mixed solvent containing water and an organic solvent so that the silane oligomer hydrate is obtained in the coating composition by the copolymerization reaction.

The immobilization layer can be formed by the method identical to that of the primer layer. That is, any wet coating method such as dipping, spraying, spin-coating, or printing can be employed, but it is not limited thereto. As shown in FIG. 1, the functional group for the immobilization layer reacts with the silanol group present on the surface of the primer layer.

The coated silane oligomer is thermoset and condensed to provide an immobilization layer having a three dimensional cross-linking structure. The thermoset temperature is preferably from 100 to 300° C. When the temperature is less than 100° C., the condensation is not sufficient, whereas when the temperature is more than 300° C., the amino group rapidly degenerates.

Figure 2:
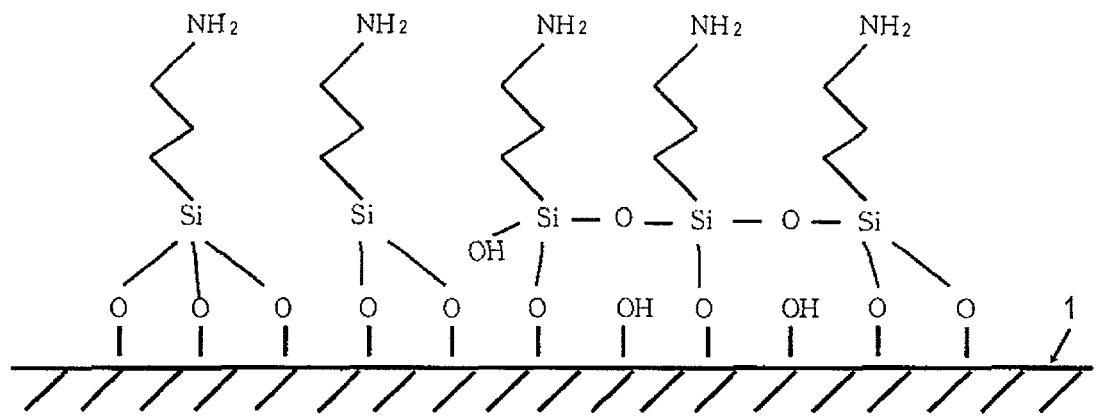
FIG. 2 is a cross-sectional view showing a conventional self-assembly-monolayer.

As shown in FIG. 2, the conventional immobilization layer formed on the substrate 1 is a self-assembly-monolayer. The self-assembly-monolayer is manufactured for an extended duration, and it is difficult to obtain a functional group with a uniform density.

Figure 3:
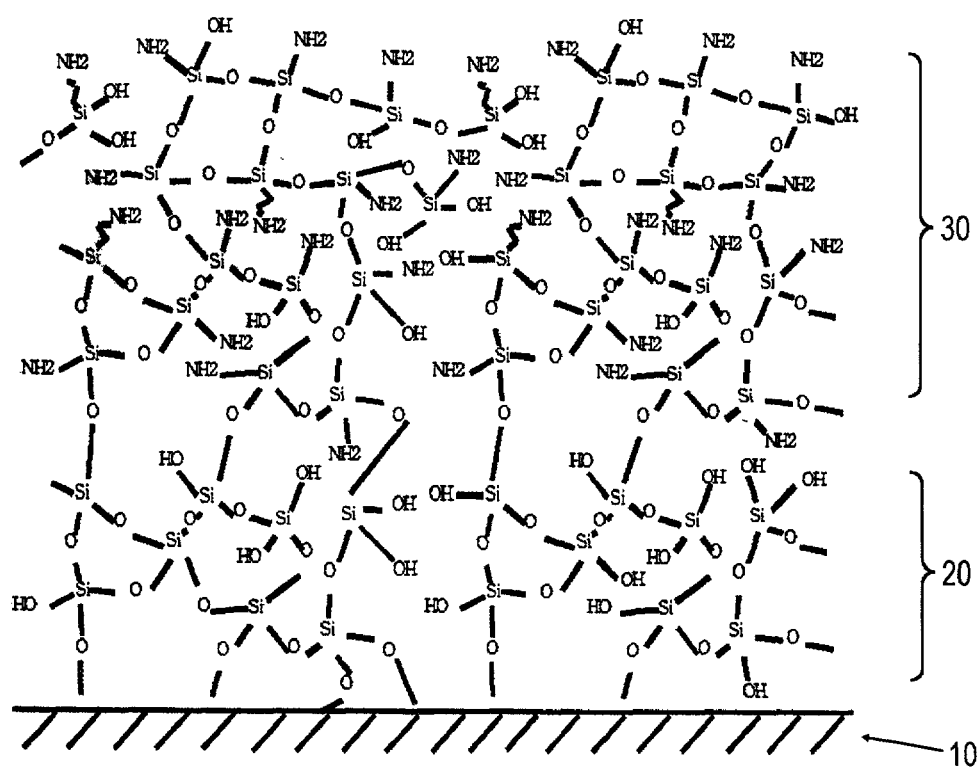
FIG. 3 is a cross-sectional view showing a substrate for immobilizing a physiological material having a three-dimensional cross-linking structure according to the present invention.

The present invention can provide the immobilization layer with a three-dimensional cross-linking structure as shown in FIG. 3, so as to provide the functional group uniformly. Further, the immobilization layer with a high-density functional group is fabricated in a relatively short time.

The three dimensional cross-linking structure prevents elimination of the immobilization layer and detachment of the physiological material when being washed with solvents used during the immobilization or washing step. Therefore, the thermal stability and reagent stability are improved due to the structural characteristics.

The primer layer present between the immobilization layer and the substrate improves the attachment between the immobilization layer and the substrate and blocks any alkaline materials which reduce the attachment strength so as to stably preserve the immobilization functional group.

The density of the immobilization group is determined by analyzing light emitted from fluorescence dye in the immobilization layer upon continuous irradiation of a laser beam, the dye being fluorescein isothiocynate (FITC) or tetraethylrhodamine isothiocynate (SCN-TMR) activated with isothiocynate or succinimide ether.

The results of the density analysis indicate that the substrate for immobilizing a physiological material according to the present invention has a very stable immobilization functional group at a uniform and high density.

The present invention also provides a biochip fabricated by attaching the physiological material to the immobilization functional group on the substrate or by attaching the physiological material activated to have a functional group onto the substrate, and washing out the unreacted physiological material to form a predetermined pattern. The physiological material is preferably reacted with the immobilization layer for 1 to 24 hours.

The term "physiological material" herein means one derived from an organism or its equivalent, or one prepared in vitro. It includes, for example, an enzyme, a protein, an antibody, a microbe, an animal and plant cell and organ, a neuron, DNA and RNA, and preferably DNA, RNA, or a protein, wherein the DNA may include cDNA, genome DNA, and an oligonucleotide; the RNA may include genome RNA, mRNA, and an oligonucleotide; and the protein may include an antibody, antigen, enzyme, peptide, etc.

The method for patterning the physiological material on the immobilization layer may be any method of photolithography, piezoelectric printing, micropipeting, spotting, etc.

Hereinafter, the present invention will be explained in detail with reference to examples. These examples, however, should not in any sense be interpreted as limiting the scope of the present invention.

EXAMPLE 1

3 g of tetraethyl orthosilicate were added to a mixture of dilution solvent including 90 g of ethanol and 7 g of water, and the pH thereof was adjusted to pH 2 by adding nitric acid, to obtain a coating composition for forming a primer layer. A slide glass was dipped into and coated with the coating composition and heated at 200° C. to form a primer layer on the slide glass. 5 g of 3-aminopropyltrimethoxysilane was mixed with 15 g of water and reacted at 60° C. for 8 hours to obtain an aminosilane oligomer hydrate. 10 g of the aminosilane oligomer hydrate were dissolved in 90 g of ethanol to provide a coating composition for forming an immobilization layer. The primer layer coated slide glass was dipped and coated in the coating composition, and then thermoset at 120° C. for 60 minutes, to form a substrate for immobilizing a physiological material.

EXAMPLE 2

3 g of tetraethyl orthosilicate and 0.3 g of bis(triethoxysilyl)ethane were added to a mixture of dilution solvent including 90 g of ethanol and 7 g of water, and the pH thereof was adjusted to pH 2 by adding nitric acid, to obtain a coating composition for forming a primer layer. A slide glass was dipped into and coated with the coating composition and heated at 200° C. to form a primer layer on the slide glass. Then, the substrate for immobilizing a physiological material was obtained by the same process as described in Example 1.

EXAMPLE 3

3 g of tetraethyl orthosilicate were added to a mixture of dilution solvent including 90 g of ethanol and 7 g of water, and the pH thereof was adjusted to pH 2 by adding nitric acid, to obtain a first coating composition for forming a primer layer. 19 g of zirconium n-butoxide were dissolved in a mixture of dilution solvent including 8 g of acetylacetone and 73 g of ethanol to provide a second coating composition for forming a primer layer. A slide glass was dipped into a coating composition mixture of the first and second coating compositions in the weight ratio of 9:1 and coated therewith, and then heated at 200° C. to form a primer layer on the slide glass. 2.5 g of 3-aminopropyltrimethoxysilane were dissolved in a mixture of dilution solvent including 7.5 g of water and 90 g of ethanol and reacted at 60° C. for 8 hours to obtain an aminosilane oligomer hydrate bearing a coating composition for forming an immobilization layer. The primer layer coated slide glass was dipped into and coated with the coating composition, then thermoset at 100° C. for 60 minutes, consequently obtaining a substrate for immobilizing a physiological material.

EXAMPLE 4

3 g of tetraethyl orthosilicate were added to a mixture of dilution solvent including 90 g of ethanol and 7 g of water, and the pH thereof was adjusted to pH 2 by adding nitric acid, to obtain a first coating composition for forming a primer layer. 17 g of titanium isopropoxide were dissolved in a mixture of dilution solvent including 6 g of acetylacetone and 77 g of ethanol to provide a second coating composition for forming a primer layer. A slide glass was dipped into a coating composition mixture of the first and second coating compositions in the weight ratio of 9:1 and coated therewith, and then heated at 200° C. to form a primer layer on the slide glass. Then, the substrate for immobilizing a physiological material was obtained by the same process as described in Example 3.

EXAMPLE 5

3 g of tetraethyl orthosilicate were added to a mixture of dilution solvent including 90 g of ethanol and 7 g of water, and the pH thereof was adjusted to pH 2 by adding nitric acid, to obtain a first coating composition for forming a primer layer. 24 g of aluminum n-butoxide were dissolved in a mixture of dilution solvent including 10 g of acetylacetone and 66 g of ethanol to provide a second coating composition for forming a primer layer. A slide glass was dipped into a coating composition mixture of the first and second coating compositions in the weight ratio of 9:1 and coated therewith, and then heated at 200° C. to form a primer layer on the slide glass. Then, the substrate for immobilizing a physiological material was obtained by the same process as described in Example 3.

EXAMPLE 6

2.5 g of aminopropyltrimethoxysilane were added to a mixted solvent including 90 g of ethanol and 7.5 g of water and reacted at 60° C. for 8 hours to obtain an aminosilane oligomer hydrate-bearing-coating composition for forming an immobilization layer. A slide glass was dipped into the coating composition and coated therewith, followed by being thermoset at 100° C. for 60 minutes, consequently obtaining a substrate for immobilizing a physiological material.

The Stability Test for the Immobilization Functional Group

Figure 4A:
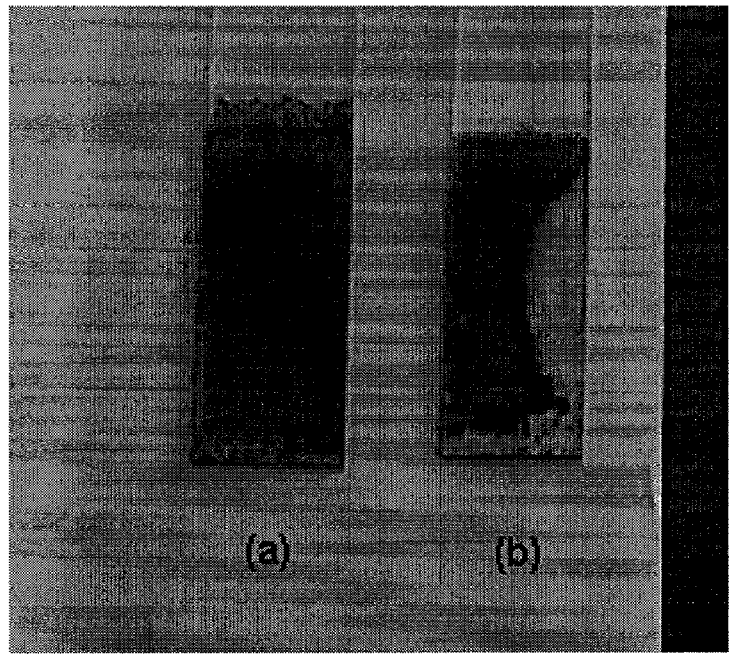
FIGS. 4A and 4B are respectively photographs showing the results of an immersion test of a substrate for immobilizing a physiological material according to Examples 1 and 2 of the present invention.
Figure 4B:
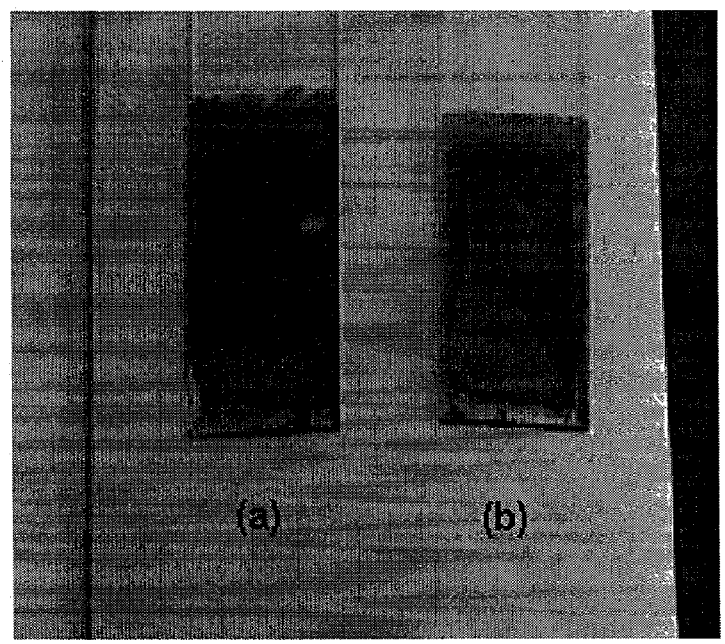

The substrates for immobilizing a physiological material fabricated by the methods according Examples 1 to 6 of the present invention were immersed in boiling water of 100° C.; for 6 hours, and colored with a dispensed solution of Au/Ag colloidal particles (available from Mitsubishi Material. Co.). FIGS. 4A and 4B are photographs of the substrates of Examples 1 and 2 before the immersion process (a) and after the lapse of 6 hours (b). As shown in FIG. 4A, in the substrate for immobilizing a physiological material according to Example 1, a degree of coloring was slightly diminished after immersion in the boiling water (b) compared with that before the immersion (a). Further, as shown in FIG. 4B, the degree of coloring of the substrate (b) according to Example 2 was almost the same as that before the immersion (a). The degree of coloring in the case of Example 6 was diminished.

The Density Determination of the Immobilization Functional Group

The substrates for immobilizing a physiological material according to Examples 1 to 6 were immersed in boiling water at 100° C. for 1 hour, and the immobilization layers were labeled with a dimethylformamide solution of FITC. A laser beam was continuously irradiated onto the immobilization layer and the light emitted from the FITC on the layer was detected by a ScanArray 4000 (manufactured by GSI LUMONICS). Table 1 shows the results thereof.

TABLE 1

|  | Fluorescence Strength (a.u.) |
|---|---|
| Example 1 | 29984 |
| Example 2 | 42189 |

TABLE 1-continued

| | Fluorescence Strength (a.u.) |
|---|---|
| Example 3 | 27775 |
| Example 4 | 25572 |
| Example 5 | 23296 |
| Example 6 | 17885 |

Generally, the higher the fluorescence strength, the more the immobilization group remains. It can be seen that the substrate for immobilizing a physiological material of the present invention can preserve the immobilization functional group at a stable and high density.

Analysis for Luminescence Image of Biochip

Figure 5A:
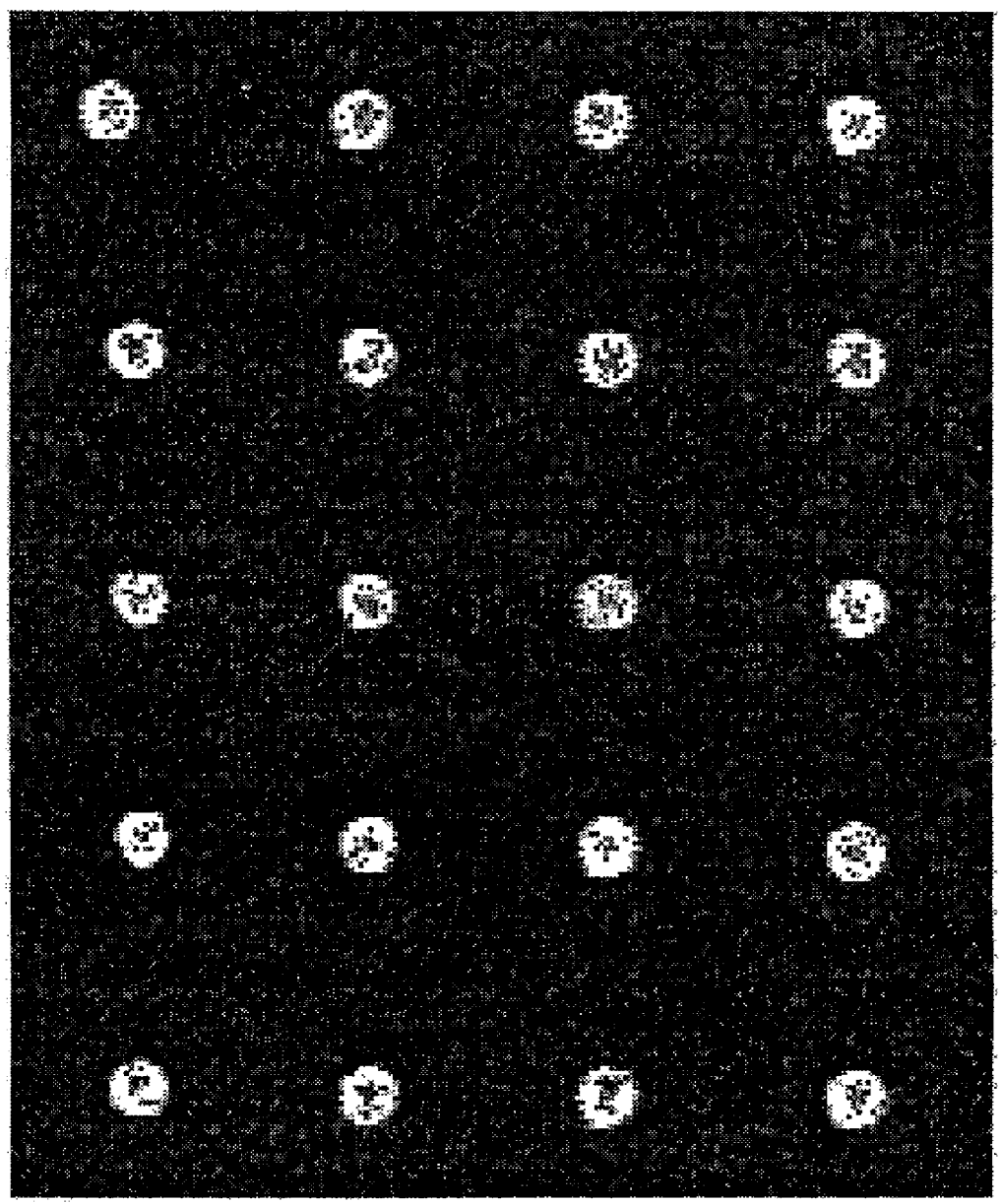
FIGS. 5A and 5B are respectively photographs showing luminescence images of substrates for immobilizing a physiological material according to Examples 1 and 6.
Figure 5B:
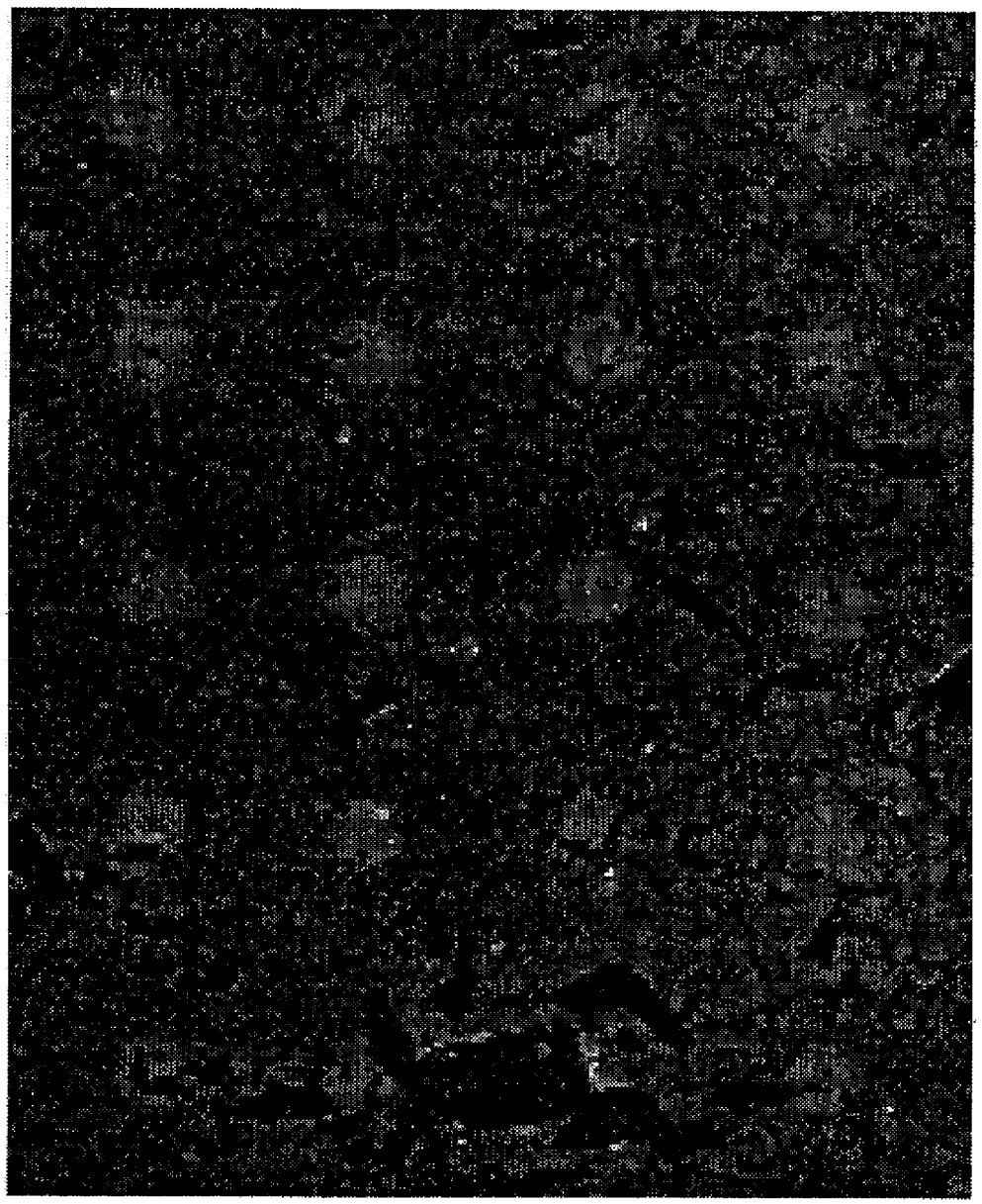

The substrates for immobilizing a physiological material according to Examples 1 to 6 were immersed in boiling water of 100° C. for one hour and reacted with a probe DNA of oligonucleotides having 15 bases, so as to immobilize the DNA on the surface. Subsequently, the substrates were immersed in a sample solution containing a target DNA labeled with fluorescence dye Cy3 (available from Amersham Pharmacia, Inc.) and reacted with the target DNA, then washed out to obtain a DNA chip. The DNA chip was irradiated with a laser beam, and the light emitted from the DNA chip was detected by a ScanArray 4000 (manufactured by GSI LUMONICS). FIGS. 5A and 5B show the luminescence images of Example 1 and Example 6, respectively.

The present invention can preserve the immobilization layer by providing a primer layer capable of enhancing the attachment between the substrate and the immobilization layer. Further, the primer layer blocks alkaline material derived from the substrate so as to stabilize the immobilization functional group. The present invention can also provide a substrate for immobilizing a physiological material having an immobilization functional group with a uniform and high density by means of a simple process.

EXAMPLE 7

5 g of 3-aminopropyltrimethoxysilane was mixed with 15 g of water and reacted at 60° C. for 8 hours to obtain an aminosilane oligomer hydrate. 10 g of the aminosilane oligomer hydrate were dissolved in 90 g of ethanol to provide an aminosilane oligomer hydrate-bearing-coating composition for forming an immobilization layer. A slide glass was dipped into and coated with the coating composition, and then thermoset at 120° C. for 60 minutes, to form a substrate for immobilizing a physiological material.

EXAMPLE 8

The substrate for immobilizing a physiological material was obtained by the same process as described in Example 7, except that 3.55 g of 3-aminopropyltirmethoxysilane and 1.45 g of methytrimethoxysilane were used instead of 3-aminopropyltrimethoxysilane.

EXAMPLE 9

The substrate for immobilizing a physiological material was obtained by the same process as described in Example 7, except that 3.55 g of 3-aminoethyltrimethoxysilane and 1.45 g of methyltrimethoxysilane were used instead of 3-aminopropyltrimethoxysilane.

COMPARATIVE EXAMPLE 1

0.1 g of aminopropyltrimethoxysilane was added to 9.9 g of toluene to obtain a coating composition for forming an immobilization layer. A slide glass was dipped into the coating composistion and coated therewith, followed by being thermoset at 120° C. for 60 minutes, consequently obtaining a substrate for immobilizing a physiological material.

The Density Determination of the Immobilization Functional Group

The substrates for immobilizing a physiological material according to Examples 7 to 9 and Comparative Example 1 were labeled with a dimethylformamide solution of FITC. A laser beam was continuously irradiated onto the immobilization layer and the light emitted from the FITC on the layer was detected by a ScanArray 4000 (manufactured by GSI LUMONICS). Table 2 shows the results thereof.

TABLE 2

| | Fluorescence Strength (a.u.) |
|---|---|
| Example 7 | 24442.04 |
| Example 8 | 34074.66 |
| Example 9 | 29708.98 |
| Comparative Example 1 | 6083.43 |

Generally, the higher the fluorescence strength, the more the immobilization group remains. As shown in Table 2, the fluorescence strengths of Examples 7 to 9 are remarkably superior to that of Comparative Example 1. It indicated that the substrate for immobilizing a physiological material of the present invention have the immobilization functional group at a density.

While the present invention has been described in detail with reference to the preferred embodiments, those skilled in the art will appreciate that various modifications and substitutions can be made thereto without departing from the spirit and scope of the present invention as set forth in the appended claims.

The invention claimed is:

1. A substrate for immobilizing a physiological material comprising a substrate material coated with a primer layer and an immobilization layer over the primer layer, the primer layer comprising a first oligomer capable of enhancing the attachment between the substrate material and the immobilization layer; and the immobilization layer comprising a second oligomer having a functional group capable of immobilizing a physiological material, wherein the primer layer comprises an oligomer formed from a mixture of compounds represented by the formula 1 and formula 2:

   (1)

   (2)

wherein

M and M' are each independently selected from the group consisting of 4B, 3A, 4A, and 5A group elements of the Periodic Table;

$R^1$ is selected from hydrogen atoms, $C_{1-20}$ alkyl groups and $C_{6-12}$ aromatic groups;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20, wherein the weight ratio of the compound of formula (1) to the compound of formula (2) ranges from 50:50 to 95:5.

2. The substrate according to claim 1, wherein:

M is selected from the group consisting of Si, Zr, Ti, Al, Sn, In, and Sb; and $R^1$ is selected from hydrogen, methyl, ethyl, propyl, butyl, and phenyl.

3. The substrate according to claim 1, wherein the compound represented by formula 1 is selected from the group consisting of silicon tetraalkoxide, aluminum tributoxide, and zirconium tetrabutoxide.

4. A substrate for immobilizing a physiological material comprising a substrate material coated with a primer layer and an immobilization layer over the primer layer, the primer layer comprising a first oligomer capable of enhancing the attachment between the substrate material and the immobilization layer; and the immobilization layer comprising a second oligomer having a functional group capable of immobilizing a physiological material, wherein the primer layer comprises an oligomer formed from a compound represented by formula 2:

$$(M'R^2{}_m)_p(R^3)_q \qquad (2)$$

wherein

M' is selected from the group consisting of 4B, 3A, 4A, and 5A group elements of the Periodic Table;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

m is a value ranging from 2 to 3 and is determined depending upon the valence of M';

p is a numerical value ranging from 2 to 4; and q is a numerical value ranging from 1 to 20.

5. The substrate according to claim 4, wherein: M' is selected from the group consisting of Si, Zr, Ti, Al, Sn, In, and Sb; and $R^2$ is selected from hydroxy, chlorine, methoxy, ethoxy, propoxy, butoxy and phenoxy.

6. The substrate according to claim 4, wherein the compound is selected from the group consisting of 1,4-bis(trimethoxysilylethyl)benzene, bis(trimethoxysilyl)hexane, bis(triethoxysilyl)methane, 1,9-bis-(trichlorosilyl)nonane, bis(tri-n-butoxytin)methane, bis(triisopropoxytitanium)hexane, and bis(triethoxysilyl) ethane.

7. A substrate for immobilizing a physiological material comprising a substrate material coated with a primer layer and an immobilization layer over the primer layer, the primer layer being deposited directly on the substrate material and comprising a first oligomer capable of enhancing the attachment between the substrate material and the immobilization layer; and the immobilization layer comprising a second oligomer having a functional group capable of immobilizing a physiological material, wherein the first oligomer of the primer layer is formed from a compound selected from compounds represented by formula 1, formula 2 and mixtures thereof:

$$M(OR^1)_n \qquad (1)$$

$$(M'R^2{}_m)_p(R^3)_q \qquad (2)$$

wherein

M and M' are each independently selected from the group consisting of 4B, 3A, 4A, and 5A group elements of the Periodic Table;

$R^1$ is selected from hydrogen atoms, $C_{1-20}$ alkyl groups and $C_{6-12}$ aromatic groups;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20;

wherein the immobilization layer comprises an oligomer formed from a compound of formula (3):

$$Y—R^4—Si(R^5)_3 \qquad (3)$$

wherein:

Y varies depending upon the terminal group of the physiological material and is at least one functional group selected from the group consisting of amino, aldehyde, mercapto, and carboxyl groups;

$R^4$ is selected from the group consisting of $C_{1-20}$ alkyl groups, $C_{6-20}$ aromatic groups, ester groups, and imine groups; and $R^5$ is selected from the group consisting of hydroxyl groups, $C_{1-20}$ alkoxy groups, acetoxy groups, halogen groups, and combinations thereof.

8. The substrate according to claim 7, wherein the compound of formula (3) is selected from the group consisting of 3-aminopropyltrirmethoxy-silane, 3-aminopropyltriethoxysilane, 2-aminoundecyltrimethoxylsilane, aminophenyltrimethoxy-silane, N-(2-aminoethylaminopropyl)trimethoxysilyl, 3-mercaptopropyltrimethoxy-silane, 3-mercaptopropyltriethoxysilane, 4-trimethoxysilylbutanal, 4-trimethoxy-silylbutanal, carboxymethyltrimethoxysilane, carboxymethyltriethoxysilane, and mixtures thereof.

9. A substrate for immobilizing a physiological material comprising a substrate material coated with a primer layer and an immobilization layer over the primer layer, the primer layer being deposited directly on the substrate material and comprising a first oligomer capable of enhancing the attachment between the substrate material and the immobilization layer; and the immobilization layer comprising a second oligomer having a functional group capable of immobilizing a physiological material, wherein the first oligomer of the primer layer is formed from a compound selected from compounds represented by formula 1, formula 2 and mixtures thereof:

$$M(OR^1)_n \qquad (1)$$

$$(M'R^2{}_m)_p(R^3)_q \qquad (2)$$

wherein:

M and M' are each independently selected from the group consisting of 4B, 3A, 4A, and 5A group elements of the Periodic Table;

$R^1$ is selected from hydrogen atoms, $C_{1-20}$ alkyl groups and $C_{6-12}$ aromatic groups;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20;

wherein the second oligomer of the immobilization layer comprises a hydrophobic silane compound having the formula (4):

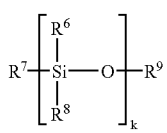

(4)

wherein $R^6$ is selected from the group consisting of $C_{1-14}$ alkyl groups, $C_{6-12}$ aromatic groups, substituted $C_{6-12}$ aromatic groups, and $CX_3$, wherein X is halogen;

$R^7$ and $R^8$ are each independently selected from the group consisting of $C_{1-14}$ alkoxy groups, acetoxy groups, hydroxyl groups, and halogen groups;

$R^9$ is selected from the group consisting of hydrogen, $C_{1-14}$ alkyl groups, and $C_{6-12}$ aromatic groups; and k is an integer ranging from 1 to 15.

10. The substrate according to claim 9, wherein $R^6$ is methyl, ethyl or propyl;

$R^7$ and $R^8$ are each independently selected from the group consisting methoxy, ethoxy, acetoxy and chlorine; and $R^9$ methyl or ethyl.

11. A coating composition for a primer layer capable of enhancing attachment between a substrate and an immobilization layer, the coating composition comprising a dilution solvent in which is dissolved a primer compound selected from compounds represented by the following formula 2:

wherein

M' is selected from the group consisting of 4B, 3A, 4A, and 5A group elements of the Periodic Table;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

m is a value ranging from 2 to 3 and is determined depending upon the valence of M';

p is a numerical value ranging from 2 to 4; and q is a numerical value ranging from 1 to 20.

12. The coating composition according to claim 11, wherein:

M' is selected from the group consisting of Si, Zr, Ti, Al, Sn, In, and Sb; and $R^2$ is selected from hydroxy, chlorine, methoxy, ethoxy, propoxy, butoxy and phenoxy.

13. The coating composition according to claim 11, wherein the compound is selected from the group consisting of 1,4-bis(trimethoxysilylethyl)benzene, bis(trimethoxysilyl)hexane, bis(triethoxysilyl)methane, 1,9-bis-(trichlorosilyl)nonane, bis(tri-n-butoxytin)methane, bis(triisopropoxytitanium)hexane, bis(triethoxysilyl) ethane, and mixtures thereof.

14. A coating composition for a primer layer capable of enhancing attachment between a substrate and an immobilization layer, the coating composition comprising a dilution solvent in which is dissolved a primer compound comprising a mixture of compounds represented by the formula 1 and formula 2:

wherein

M and M' are each independently selected from the group consisting of 4B, 3A, 4A, and 5A group elements of the Periodic Table;

$R^1$ is selected from hydrogen atoms, $C_{1-20}$ alkyl groups and $C_{6-12}$ aromatic groups;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20, wherein the weight ratio of the compound of formula (1) to the compound of formula (2) ranges from 50:50 to 95:5.

15. The coating composition according to claim 11, wherein the dilution solvent is at least one selected from the group consisting of alcohol solvents, cellusolve solvents and acetones.

16. A coating composition for an immobilization layer for a substrate, the coating composition comprising a dilution solvent comprising water in which is dissolved a compound selected from compounds represented by the formula (3):

wherein:

Y varies depending upon the terminal group of the physiological material and is at least one functional group selected from the group consisting of amino, aldehyde, mercapto, and carboxyl groups;

$R^4$ is selected from the group consisting of $C_{1-20}$ alkyl groups, $C_{6-20}$ aromatic groups, ester groups, and imine groups; and $R^5$ is selected from the group consisting of hydroxyl groups, $C_{1-20}$ alkoxy groups, acetoxy groups, halogen groups, and combinations thereof, the coating composition further comprising a hydrophobic silane compound dissolved in a dilution solvent, the hydrophobic silane compound having the formula (4):

(4)

wherein $R^6$ is selected from the group consisting of $C_{1-14}$ alkyl groups, $C_{6-12}$ aromatic groups, substituted $C_{6-12}$ aromatic groups, and $CX_3$, wherein X is halogen;

$R^7$ and $R^8$ are each independently selected from the group consisting of $C_{1-14}$ alkoxy groups, acetoxy groups, hydroxyl groups, and halogen groups;

R⁹ is selected from the group consisting of hydrogen, $C_{1-14}$ alkyl groups, and $C_{6-12}$ aromatic groups; and k is an integer ranging from 1 to 15.

17. The coating composition according to claim 16, wherein

R⁶ is methyl, ethyl or propyl;

R⁷ and R⁸ are each independently selected from the group consisting methoxy, ethoxy, acetoxy and chlorine; and R⁹ methyl or ethyl.

18. The coating composition of claim 16, wherein the weight ratio of the compound of formula (3) to the compound of formula (4) is 50:50 to 95:5.

19. A biochip comprising a physiological material immobilized on a surface of the substrate according to claim 4.

20. A biochip according to claim 19, wherein the physiological material is selected from the group consisting of enzymes, proteins, DNA, RNA, microbes, microorganisms, animal and plant cells and organs, and neurons.

21. A method for making a substrate for immobilizing a physiological material, the method comprising:

forming a primer layer directly on a substrate material by coating onto the substrate material a primer layer coating composition comprising a dilution solvent in which is dissolved a compound being capable of enhancing the attachment between the substrate material and an immobilization layer to form a primer coated substrate, the primer layer coating composition comprising a mixture of compounds represented by the following formula 1 and formula 2:

$$M(OR^1)_n \quad (1)$$

$$(M'R^2_m)_p(R^3)_q \quad (2)$$

wherein

M and M' are each independently selected from the group consisting of 4B, 3A, 4A, and 5A group elements of the Periodic Table;

R¹ is selected from hydrogen atoms, $C_{1-20}$ alkyl groups and $C_{6-12}$ aromatic groups;

R² is selected from hydroxy, halogen atoms, $C_{1-20}$ alkoxy groups and $C_{6-12}$ oxyaromatic groups;

R³ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20;

forming the immobilization layer by coating onto the primer layer an immobilization layer coating composition comprising a dilution solvent in which is dissolved a compound having a functional group capable of immobilizing a physiological material to form an immobilization coated substrate.

22. The method according to claim 21, wherein:

M and M' are each independently selected from the group consisting of Si, Zr, Ti, Al, Sn, In, and Sb; and R¹ is selected from hydrogen, methyl, ethyl, propyl, butyl, and phenyl; and R² is selected from hydroxy, chlorine, methoxy, ethoxy, propoxy, butoxy and phenoxy.

23. A method for making a substrate for immobilizing a physiological material, the method comprising:

forming a primer layer directly on a substrate material by coating onto the substrate material a primer layer coating composition comprising a dilution solvent in which is dissolved a compound being capable of enhancing the attachment between the substrate material and an immobilization layer to form a primer coated substrate, the primer layer coating composition comprising a compound selected from compounds represented by the following formula 1 and formula 2 and mixtures thereof:

$$M(OR^1)_n \quad (1)$$

$$(M'R^2_m)_p(R^3)_q \quad (2)$$

wherein:

M and M' are each independently selected from the group consisting of 4B, 3A, 4A, and 5A group elements of the Periodic Table;

R¹ is selected from hydrogen atoms, $C_{1-20}$ alkyl groups and $C_{6-12}$ aromatic groups;

R² is selected from hydroxy, halogen atoms, $C_{1-20}$ alkoxy groups and $C_{6-12}$ oxyaromatic groups;

R³ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and q is a numerical value ranging from 1 to 20;

forming the immobilization layer by coating onto the primer layer an immobilization layer coating composition comprising a dilution solvent in which is dissolved a compound having a functional group capable of immobilizing a physiological material to form an immobilization coated substrate, wherein the immobilization layer coating composition comprises a compound of formula (3):

$$Y-R^4-Si(R^5)_3 \quad (3)$$

wherein:

Y varies depending upon the terminal group of the physiological material and is at least one functional group selected from the group consisting of amino, aldehyde, mercapto, and carboxyl groups;

R⁴ is selected from the group consisting of $C_{1-20}$ alkyl groups, $C_{6-20}$ aromatic groups, ester groups, and imine groups; and R⁵ is selected from the group consisting of hydroxyl groups, $C_{1-20}$ alkoxy groups, acetoxy groups, halogen groups, and combinations thereof.

24. The method according to claim 23, wherein the primer layer coating composition comprises a compound represented by formula 1.

25. A method for making a substrate for immobilizing a physiological material, the method comprising:

forming a primer layer on a substrate material by coating onto the substrate material a primer layer coating composition comprising a dilution solvent in which is dissolved a compound being capable of enhancing the attachment between the substrate material and an immobilization layer to form a primer coated substrate, the primer layer coating composition comprising a compound selected from compounds represented by the following formula 2:

$$(M'R^2_m)_p(R^3)_q \quad (2)$$

wherein

M' is selected from the group consisting of 4B, 3A, 4A, and 5A group elements of the Periodic Table;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

m is a value ranging from 2 to 3 and is determined depending upon the valence of M';

p is a numerical value ranging from 2 to 4; and q is a numerical value ranging from 1 to 20;

forming the immobilization layer by coating onto the primer layer an immobilization layer coating composition comprising a dilution solvent in which is dissolved a compound having a functional group capable of immobilizing a physiological material to form an immobilization coated substrate.

26. A method for making a substrate for immobilizing a physiological material, the method comprising:

forming a primer layer directly on a substrate material by coating onto the substrate material a primer layer coating composition comprising a dilution solvent in which is dissolved a compound being capable of enhancing the attachment between the substrate material and an immobilization layer to form a primer coated substrate, the primer layer coating composition comprising a compound selected from compounds represented by the following formula 1 and formula 2 and mixtures thereof:

wherein:

M and M' are each independently selected from the group consisting of 4B, 3A, 4A, and 5A group elements of the Periodic Table;

$R^1$ is selected from hydrogen atoms, $C_{1-20}$ alkyl groups and $C_{6-12}$ aromatic groups;

$R^2$ is selected from hydroxy, halogen atoms, $C_{1-20}$ alkoxy groups and $C_{6-12}$ oxyaromatic groups;

$R^3$ is a methylene or a phenyl group, optionally substituted with a $C_{1-6}$ substituent;

n is a value ranging from 3 to 4 and is determined depending upon the valence of M;

m is a value ranging from 2 to 3 and is determined depending upon the valence of M';

p is a numerical value ranging from 2 to 4; and g is a numerical value ranging from 1 to 20;

forming the immobilization layer by coating onto the primer layer an immobilization layer coating composition comprising a dilution solvent in which is dissolved a compound having a functional group capable of immobilizing a physiological material to form an immobilization coated substrate, wherein the immobilization layer coating composition comprises a hydrophobic silane compound having the formula (4):

wherein $R^6$ is selected from the group consisting of $C_{1-14}$ alkyl groups, $C_{6-12}$ aromatic groups, substituted $C_{6-12}$ aromatic groups, and $CX_3$, wherein X is halogen;

$R^7$ and $R^8$ are each independently selected from the group consisting of $C_{1-14}$ alkoxy groups, acetoxy groups, hydroxyl groups, and halogen groups;

$R^9$ is selected from the group consisting of hydrogen, $C_{1-14}$ alkyl groups, and $C_{6-12}$ aromatic groups; and k is an integer ranging from 1 to 15.

27. The method according to claim 23, wherein:

M and M' are each independently selected from the group consisting of Si, Zr, Ti, Al, Sn, In, and Sb; and $R^1$ is selected from hydrogen, methyl, ethyl, propyl, butyl, and phenyl; and $R^2$ is selected from hydroxy, chlorine, methoxy, ethoxy, propoxy, butoxy and phenoxy.

28. The method according to claim 26, wherein:

M and M' are each independently selected from the group consisting of Si, Zr, Ti, Al, Sn, In, and Sb; and $R^1$ is selected from hydrogen, methyl, ethyl, propyl, butyl, and phenyl; and $R^2$ is selected from hydroxy, chlorine, methoxy, ethoxy, propoxy, butoxy and phenoxy.

29. The method according to claim 26, wherein the primer layer coating composition comprises a compound represented by formula 1.

30. A biochip comprising a physiological material immobilized on a surface of a substrate according to claim 1.

31. A biochip according to claim 30, wherein the physiological material is selected from the group consisting of enzymes, proteins, DNA, RNA, microbes, microorganisms, animal and plant cells and organs, and neurons.

* * * * *

UNITED STATES PATENT AND TRADEMARK OFFICE
CERTIFICATE OF CORRECTION

PATENT NO. : 7,097,882 B2  Page 1 of 1
APPLICATION NO. : 10/107721
DATED : August 29, 2006
INVENTOR(S) : Seo et al.

It is certified that error appears in the above-identified patent and that said Letters Patent is hereby corrected as shown below:

In the Claims

| | |
|---|---|
| Column 14, line 35, Claim 8 | Delete "3-aminopropyltrirmethoxy-silane", Insert --3-aminopropyltrimethoxysilane-- |
| Column 14, line 38, Claim 8 | Delete "methoxysilyl", Insert --methoxysilane-- |
| Column 15, line 33, Claim 10 | After "$R^9$", Insert --is-- |
| Column 15, line 60, Claim 13 | Delete "bis(triethoxysilyl)methane", Insert --bis(triethyoxysilyl)methane-- |
| Column 17, line 9, Claim 17 | After "$R^9$" Insert --is-- |
| Column 19, line 44, Claim 26 | Delete "g is a", Insert --q is a-- |

Signed and Sealed this

Seventeenth Day of July, 2007

JON W. DUDAS
*Director of the United States Patent and Trademark Office*